(12) United States Patent
Dalgleish et al.

(10) Patent No.: US 11,304,943 B2
(45) Date of Patent: Apr. 19, 2022

(54) COMBINATION FOR USE IN THE TREATMENT OF LUNG CANCER

(71) Applicant: LDN Pharma Limited, London (GB)

(72) Inventors: Angus Dalgleish, London (GB); Wai Lui, London (GB)

(73) Assignee: LDN PHARMA LIMITED, London (GB)

( * ) Notice: Subject to any disclaimer, the term of this patent is extended or adjusted under 35 U.S.C. 154(b) by 0 days.

(21) Appl. No.: 16/499,168

(22) PCT Filed: Mar. 28, 2018

(86) PCT No.: PCT/GB2018/050820
§ 371 (c)(1),
(2) Date: Sep. 27, 2019

(87) PCT Pub. No.: WO2018/178668
PCT Pub. Date: Oct. 4, 2018

(65) Prior Publication Data
US 2020/0101064 A1 Apr. 2, 2020

(30) Foreign Application Priority Data
Mar. 28, 2017 (GB) ..................................... 1704909

(51) Int. Cl.
*A61K 31/485* (2006.01)
*A61P 35/00* (2006.01)
*A61K 31/59* (2006.01)
*A61K 45/06* (2006.01)

(52) U.S. Cl.
CPC ............ *A61K 31/485* (2013.01); *A61K 31/59* (2013.01); *A61P 35/00* (2018.01); *A61K 45/06* (2013.01)

(58) Field of Classification Search
CPC .. A61K 31/592; A61K 31/593; A61K 31/436; A61K 31/485; A61P 35/00
See application file for complete search history.

(56) References Cited

U.S. PATENT DOCUMENTS

| | | | |
|---|---|---|---|
| 4,689,332 A | 8/1987 | McLaughlin et al. | |
| 6,384,044 B1 | 5/2002 | Bihari et al. | |
| 9,885,438 B2 * | 2/2018 | Eads | F24F 13/222 |
| 2006/0172014 A1 * | 8/2006 | Curd | A61K 45/06 424/649 |
| 2009/0191185 A1 | 7/2009 | Selander et al. | |
| 2010/0152221 A1 * | 6/2010 | Liang | A61K 31/485 514/282 |

FOREIGN PATENT DOCUMENTS

| | | |
|---|---|---|
| CN | 1294519 A | 5/2001 |
| CN | 1802349 A | 7/2006 |
| CN | 101237886 A | 8/2008 |
| CN | 101321554 A | 12/2008 |
| CN | 104936581 A | 9/2015 |
| JP | 2001-511818 A | 8/2001 |
| JP | 2008-535850 A | 9/2008 |
| JP | 2015-107918 A | 6/2015 |
| WO | 2015/189597 A1 | 12/2015 |
| WO | WO-2015189597 A1 * | 12/2015 ........... A61K 31/282 |
| WO | 2016/061531 A1 | 4/2016 |

OTHER PUBLICATIONS

Norton et al., "Vitamin D: Potential in the Prevention and Treatment of Lung Cancer," Anticancer Research, 32:211-222, 2012.
Opravz, Petra, Written Opinion of the International Searching Authority, PCT/GB2018/050820, European Patent Office, dated Jun. 6, 2018.
Wang, Sihui, China National Intellectual Property Administration, Application No. 201880035454.9, dated May 28, 2021.
Yan, Ling-di et al., "Pharmacokinetics of 6β-naltrexol after single and multiple intramuscular injections in Beagle dogs", Acta Pharmaceutica Sinica, Jul. 2009, 44 (7): 722-725.
Gerald Marie, European Patent Office, EP14 725 506.1, Examination Report, dated Aug. 19, 2021.
Umeda, Takashi, Office Action, Application No. 2020-503373, Japan Patent Office, dated Jan. 11, 2022.

* cited by examiner

*Primary Examiner* — Theodore R. Howell
*Assistant Examiner* — George W Kosturko
(74) *Attorney, Agent, or Firm* — Gavrilovich, Dodd & Lindsey LLP

(57) ABSTRACT

The invention is based on the finding that co-administration of 6-β-naltrexol alongside vitamin D together with a chemotherapeutic agent, results in a further reduction in lung cancer cell growth. The combination of 6-β-naltrexol with vitamin D results in a greater decrease in the growth of cancer cells compared to the sum of the effects of each agent when administered in isolation.

14 Claims, 2 Drawing Sheets

COMBINATION FOR USE IN THE TREATMENT OF LUNG CANCER

CROSS REFERENCE TO RELATED APPLICATIONS

This application is a U.S. National Stage Application filed under 35 U.S.C. § 371 and claims priority from International Application No. PCT/GB2018/050820, filed Mar. 28, 2019, which application claims the benefit of Great Britain Application No. 1704909.9, filed Mar. 28, 2017, the disclosures of which are incorporated herein in their entirety by reference.

FIELD OF THE INVENTION

The invention relates to compounds for use in the treatment of lung cancer and methods of treatment of lung cancer comprising administration of said compounds.

BACKGROUND OF THE INVENTION

In 2012 lung cancer resulted in approximately 20% of all cancer-related deaths worldwide, and was the most common cancer-related cause of death in men. Subjects with lung cancer currently have the second lowest five-year survival rate of any cancer subgroup in the United Kingdom. Typically, for all patients diagnosed with lung cancer, only 10% will survive for five years or more following diagnosis. The individual survival rate depends on the stage at which diagnosis is made and the type of lung cancer that is present.

The vast majority of lung cancers are caused by long-term tobacco smoking, whereas a small minority of cases arise in subjects who have never smoked. There are several hereditary mutations that can predispose subjects to developing lung cancer, while other environmental factors, such as exposure to air pollution, radon gas, second-hand smoke or asbestos also increase the risk of developing the disease. As the majority of risk factors associated with the development of lung cancer are environmental, the average age of subjects diagnosed with lung cancer is in excess of 70 years of age.

At present, there are no effective high-throughput screening methods for detecting the presence of lung cancer before the onset of symptoms. Pre-symptomatic diagnosis would enable therapeutic intervention at an early stage and thus increase the likelihood of survival. However, the majority of lung cancers are diagnosed at a mid-to-late stage. This is largely due to the similarity of symptoms associated with lung cancer and those already experienced by smokers, which can lead to a substantial delay in diagnosis.

Lung cancer develops when carcinogens present in air pollutants cause mutations in DNA that activate proto-oncogenes such as K-ras or EGFR or inactivate tumour suppressor genes such as p53. Typically, lung cancer is treated either by surgical methods, chemotherapy, or radiotherapy, or any combination of the above. There are also a small number of targeted lung cancer therapies emerging on to the market.

Nevertheless, the survival rate of lung cancer subjects needs to be improved, and one way in which this can be achieved is to develop new therapies.

Thus, there is an on-going need for developing effective treatments for lung cancer.

SUMMARY OF THE INVENTION

The invention is based on the finding that co-administration of 6-β-naltrexol alongside vitamin D together with a chemotherapeutic agent, results in a further reduction in lung cancer cell growth. The combination of 6-β-naltrexol with vitamin D results in a greater decrease in the growth of cancer cells compared to the sum of the effects of each agent when administered in isolation.

The invention is predicated on the discovery that 6-β-naltrexol operates by a cytostatic mechanism, as opposed to causing cytotoxicity, the latter being the mechanism by which the 6-β-naltrexol precursor naltrexone mediates anti-cancer activity. Moreover, the differential effects of 6-β-naltrexol and naltrexone are achieved at equivalent doses. Importantly, at the dosage regime relevant to the invention, the particular metabolic pathway activated when naltrexone is administered to subjects for the treatment of cancer precludes the formation of substantial quantities of 6-β-naltrexol within the human body.

Accordingly, in a first aspect of the invention there is provided 6-β-naltrexol, for sequential, separate or simultaneous administration with vitamin D or an active metabolite thereof for use in the treatment of a subject having lung cancer for use in the treatment of a subject having lung cancer.

In a second aspect of the invention, there is provided a method for the treatment of a subject having lung cancer, comprising administering a therapeutically-effective amount of 6-β-naltrexol, wherein the subject is also administered vitamin D or an active metabolite thereof.

DESCRIPTION OF THE DRAWINGS

The invention is further defined by reference to the following drawings, in which.

DETAILED DESCRIPTION OF THE INVENTION

Figure 1:
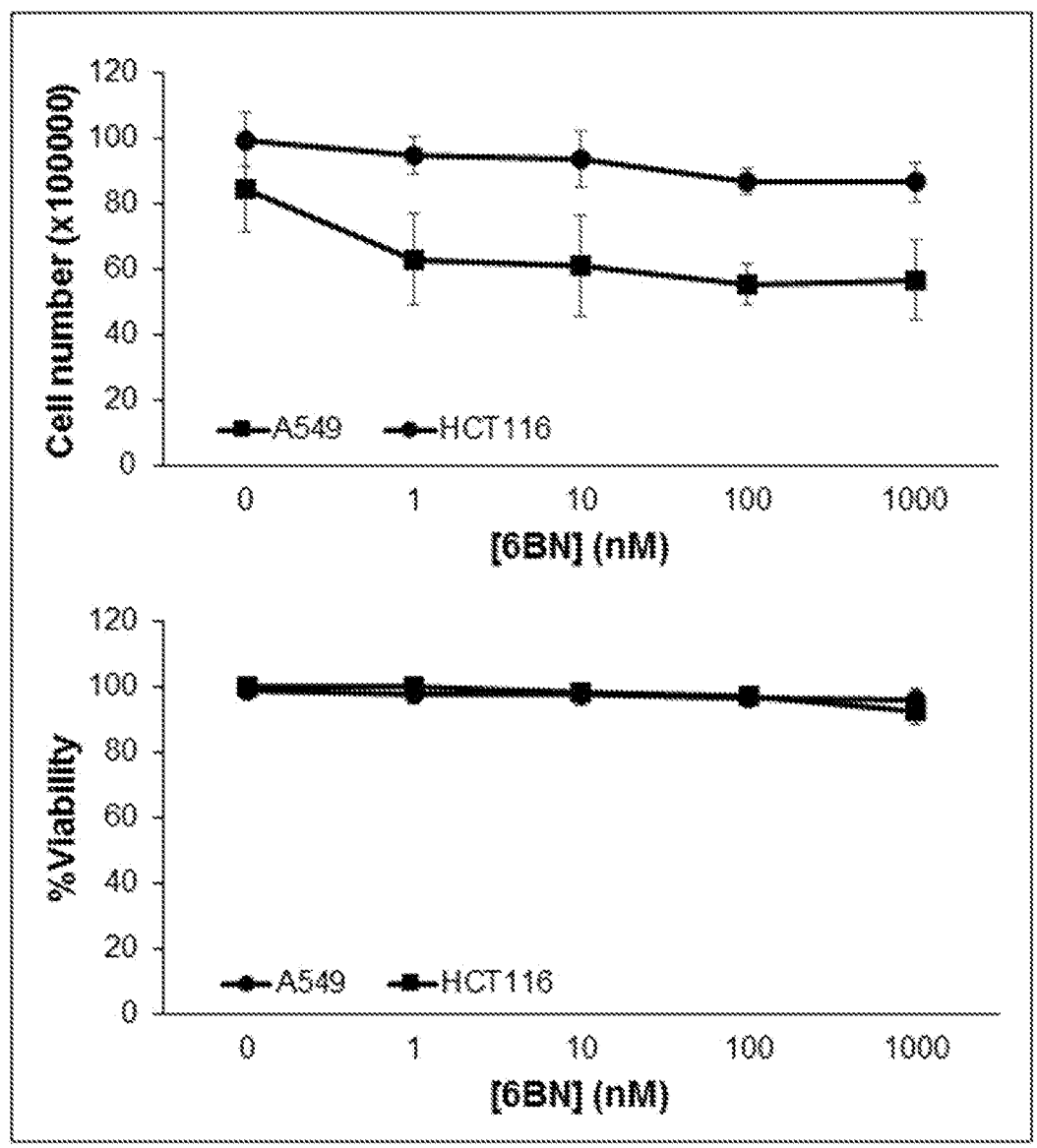
FIG. 1 shows the effect of 6-β-naltrexol (6BN) and naltrexone (NTX) on A549 (lung cancer) and HCT116 (colorectal cancer) cell numbers when administered at drug concentrations of 0.001 µM, 0.01 µM, 0.1 µM or 1 µM. Experiments were performed alongside a control where cells were not administered with 6-β-naltrexol or naltrexone (0).

The invention is based on the finding that administration of 6-β-naltrexol at a particular dosage regime is effective in arresting the growth of lung cancer cells. 6-β-naltrexol has also been shown to have a synergistic effect when administered in combination with other chemotherapeutic agents and other agents, such as vitamin D.

Importantly, administration of 6-β-naltrexol leads to a reduction in cell growth but does not cause cytotoxicity. It is therefore envisaged that administration of 6-β-naltrexol in the specified regime will only target cells that are undergoing proliferation, whilst leaving somatic cells unaffected. Administration of a drug that targets only the cells of the disease will likely lead to a substantial reduction in the off-target effects that are observed when anti-cancer agents that operate via cytotoxic mechanisms are administered. Thus, administration of 6-β-naltrexol in combination with other anti-cancer agents will increase therapeutic efficacy and reduce the inherent harsh side-effects that often result from combining traditional anti-cancer agents in therapies. Furthermore, it is envisaged that administration of 6-β-naltrexol in a combination therapy will enable the second anti-cancer agent to be administered in a greater dose, owing to the minimal side-effects that result from administration of an agent that only targets proliferating cells of the disease.

The invention can be further understood with reference to the following definitions:

As used herein "6-β-naltrexol" refers to 17-(Cyclopropylmethyl)-4,5-epoxymorphinan-3,6beta,14-triol (cas No. 49625-89-0) and pharmaceutically acceptable salts, solvates, hydrates, stereoisomers, clathrates and prodrugs thereof. 6-β-naltrexol is an active metabolite of naltrexone. The term 6-β-naltrexol also encompasses functionally equivalent analogues thereof and metabolites, and pharmaceutically acceptable salts of any of the above, that retain functional equivalence with respect to the novel uses of 6-β-naltrexol embodied within the invention.

As used herein, "chemotherapeutic agent" has its conventional meaning used in the art. For the purposes of the present invention the term chemotherapeutic agent is encompassed within the phrase "anti-cancer agent".

As used herein, the term "subject" refers to any animal (for example, a mammal), including, but not limited to, humans, non-human primates, canines, felines, rodents, and the like, which is to be the recipient of a treatment in which 6-β-naltrexol is to be used according to the present invention. Typically, the terms "subject" and "patient" are used interchangeably herein in reference to a human subject.

As used herein, the terms "treating" and "treatment" and "to treat" refer to both 1) therapeutic measures that cure, slow down, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In some instances, a subject is successfully "treated" for a tumour/cancer according to the present invention if the subject shows one or more of the following: a reduction in the number of, or complete absence of, cancer cells; a reduction in the tumour size; inhibition of, or an absence of, cancer cell infiltration into peripheral organs including, for example, the spread of cancer into soft tissue and bone; inhibition of, or an absence of, tumour metastasis; inhibition of, or an absence of, tumour growth; reduced morbidity and mortality; reduction in tumourigenicity, tumourigenic frequency, or tumourigenic capacity of a tumour; reduction in the number or frequency of cancer stem cells in a tumour; differentiation of tumourigenic cells to a non-tumourigenic state; or some combination of effects.

As used herein, the term "tumour/cancer" refers to any mass of tissue that results from excessive cell growth, proliferation and/or survival, either benign (noncancerous) or malignant (cancerous), including pre-cancerous lesions. The terms "tumour/cancer" and "neoplasm" may be used interchangeably. Tumours and cancers include benign, malignant, metastatic and non-metastatic types, and include any stage (I, II, Ill, IV or V) or grade (G1, G2, G3, etc.) of tumour, or cancer, or metastasis that is progressing, worsening, stabilized or in remission.

According to a first aspect of the invention, there is provided 6-β-naltrexol for simultaneous, separate or sequential administration with vitamin D or an active metabolite thereof for use in the treatment of a subject having lung cancer.

As used herein, "vitamin D" refers to vitamin D and any intermediate or product of a metabolic pathway of vitamin D that result in a metabolite that is capable of boosting the cytostatic effect of 6-β-naltrexol. Metabolite may refer to a vitamin D precursor, which can be incorporated into a vitamin D synthetic pathway occurring naturally within the subject to undergo the therapy of the invention. Alternatively, metabolite may refer to a molecule derived from an anabolic or catabolic process that utilizes vitamin D. Non-limiting examples of vitamin D metabolites include ergocalciferol, cholecalciferol, calcidiol, and calcitriol, 1a-hydroxycholecalciferol, 25-hydroxycholecalciferol, 1a,25-hydroxycholecalciferol, 24,25-hydroxycholecalciferol. An "active" metabolite is a metabolite that can be used in the context of the present invention. Dosage regimes of vitamin D or active metabolites thereof will be well known to the person skilled in the art. The term vitamin D also encompasses pharmaceutically acceptable salts of any of the above. A particularly suitable metabolite of vitamin D for use in the present invention is calcitriol. The inventors have shown that concurrent administration of calcitriol together with a particular dose of 6-β-naltrexol enhances the cytostatic effect of 6-β-naltrexol. Calcitriol appears to have no independent cytostatic effect when administered to lung cancer cells in isolation.

As used herein, the terms "concurrent administration" or "concurrently" or "simultaneous", "sequential" or "separate" mean that administration of 6-β-naltrexol and the vitamin D product occur as part of the same treatment regimen.

"Simultaneous" administration, as defined herein, includes the administration of 6-β-naltrexol and the vitamin D product within about 2 hours or about 1 hour or less of each other, even more preferably at the same time.

"Separate" administration, as defined herein, includes the administration of 6-β-naltrexol and the vitamin D product, more than about 12 hours, or about 8 hours, or about 6 hours or about 4 hours or about 2 hours apart.

"Sequential" administration, as defined herein, includes the administration of 6-β-naltrexol and the vitamin D product each in multiple aliquots and/or doses and/or on separate occasions. 6-β-naltrexol may be administered to the patient before or after administration of the vitamin D product. Alternatively, the vitamin D product is continued to be applied to the patient after treatment with 6-β-naltrexol ceases.

In another embodiment, the 6-β-naltrexol and the vitamin D are administered simultaneously.

In one embodiment, the vitamin D product is to be administered to the patient in an amount sufficient to bring the subject's blood vitamin D concentration to at least 40 ng/ml, more preferable at least 50 ng/ml. Preferably, the blood vitamin D concentration is raised to within a range of from 40 to 220 ng/ml, more preferably the blood vitamin D concentration is raised to within a range of from 40 to 90 ng/ml.

A sufficient amount can be determined by the skilled person by making a routine assessment of certain parameters of the patient to undergo the administration, such as, but not limited to, age, weight, gender, history of illness and/or other lifestyle factors including smoking, alcohol consumption and the level of exercise. Furthermore the skilled person can ascertain whether a dose has been sufficient to raise the vitamin D blood concentration to a sufficient amount by performing routine biochemical and analytical assays on a biological sample obtained from the subject. Preferably, the sample upon which said analysis is to be performed is blood.

Examples of such well known assays include but are not limited to mass spectrometry, where the level of vitamin D or active metabolites thereof can be quantitatively measured. A sufficient amount is therefore an amount that achieves the desired blood vitamin D concentration. The desired concentration can be achieved after single administration or after repeated administrations of a dose of vitamin D or an active metabolite thereof. Where the vitamin D product and the 6-β-naltrexol product are to be administered simultaneously, it is immaterial whether the vitamin D blood concentration is within the desired range prior to administration of the 6-β-naltrexol product, provided that the vitamin D product is administered in an amount sufficient to raise the blood vitamin D concentration to within the desired concentration range. Other methods for determining the concentration of vitamin D or active metabolites thereof within a biological sample obtained from the patient will be well known to the skilled person. In certain embodiments, the amount of the vitamin D sufficient to raise the blood vitamin D concentration to beyond a certain level is referred to as the "therapeutically effective amount" of the vitamin D product. In another embodiment, the 6-β-naltrexol is for use in a subject, wherein the subject is undergoing or is selected to undergo treatment with an anti-cancer agent.

Further according to said first aspect, the anti-cancer agent may be selected from the group consisting of PI3-kinase inhibitors, AKT inhibitors, taxanes, antimetabolites, alkylating agents, cell cycle inhibitors, topoisomerase inhibitors and cytotoxic antibodies. The anti-cancer agent can be administered in any conventional way, the method of administration being largely dependent on the anti-cancer agent to be used. Accordingly, administration by inter alia, the parenteral, oral, sublingual, nasal and/or pulmonary routes are envisaged.

Where the anti-cancer agent is a PI3-kinase inhibitor, suitable examples include, but are not limited to, wortmannin, LY294002, demethoxyviridin, IC87114, NVP-BEZ235, BAY 80-6946, BKM120, GDC-0941, GDC-9080; including combinations thereof; and pharmaceutically acceptable salts, solvates, hydrates, stereoisomers, clathrates and prodrugs of any of the above.

Where the anti-cancer agent is an AKT inhibitor, suitable examples include, but are not limited to, MK-2206, GSK690693, perifosine, PHT-427, AT7867, honokiol, PF-04691502; including combinations thereof; and pharmaceutically acceptable salts, solvates, hydrates, stereoisomers, clathrates and prodrugs of any of the above.

Where the anti-cancer agent is a taxane, suitable examples include, but are not limited to, paclitaxel and docetaxel; including combinations thereof; and pharmaceutically acceptable salts, solvates, hydrates, stereoisomers, clathrates and prodrugs of any of the above.

Where the anti-cancer agent is an antimetabolite, suitable examples include, but are not limited to, methotrexate, 5-fluorouracil, capecitabin, cytosinarabinoside (Cytarabin), gemcitabine, 6-thioguanin, pentostatin, azathioprin, 6-mercaptopurin, fludarabin and cladribin; including combinations thereof; and pharmaceutically acceptable salts, solvates, hydrates, stereoisomers, clathrates and prodrugs of any of the above. Gemcitabine is an especially preferred antimetabolite. By way of example, gemcitabine may be administered at a dose (per administration) of 800-1200 mg/m$^2$, preferably 900-1100 mg/m$^2$, for example about 1000 mg/m$^2$, or 1000 mg/m$^2$.

Where the anti-cancer agent is an alkylating agent, suitable examples include, but are not limited to, mechlorethamine, cyclophosphamide, ifosfamide, trofosfamide, melphalan (L-sarcolysin), chlorambucil, hexamethylmelamine, thiotepa, busulfan, carmustine (BCNU), streptozocin (streptozotocin), dacarbazine (DTIC; dimethyltriazenoimidazol ecarboxamide) temozolomide and oxaliplatin; including combinations thereof; and pharmaceutically acceptable salts, solvates, hydrates, stereoisomers, clathrates and prodrugs of any of the above. Cyclophosphamide and oxaliplatin are especially preferred alkylating agents. By way of example, oxaliplatin may be administered at a dose (per administration) of 65-105 mg/m$^2$, preferably 75-95 mg/m$^2$, for example about 85 mg/m$^2$, or 85 mg/m$^2$. By way of example, cyclophosphamide may be administered at a dose (per administration) of up to 1800 mg/m$^2$, for example 400-1800 mg/m$^2$.

Where the anti-cancer agent is a cell cycle inhibitor, suitable examples include, but are not limited to, Epothilone, Vincristine, Vinblastine, staurosporine/UCN-01, 17AAG, XL844, CHIR-124, PF-00477736, CEP-3891, Flavopiridol, berberine, P276-00, terameprocol, isoflavone daidzein, BI2536, BI6727, GSK461364, Cyclapolin, ON-01910, NMS-P937, TAK-960, Ispinesib, Monastrol, AZD4877, LY2523355, ARRY-520, MK-0731, SB743921, GSK923295, Lonafarnib, proTAME, Bortezomib, MLN9708, ONX0912, CEP-18770; including combinations thereof; and pharmaceutically acceptable salts, solvates, hydrates, stereoisomers, clathrates and prodrugs of any of the above; particularly suitable examples of cell cycle inhibitors include, but are not limited to, Hespaeradin, ZM447439, VX-680, MLN-8054, PHA-739358, AT-9283, AZD1152, MLN8237, ENMD2076, SU6668; including combinations thereof; and other inhibitors of Aurora kinases; and pharmaceutically acceptable salts, solvates, hydrates, stereoisomers, clathrates and prodrugs of any of the above. Preferably, the cell cycle inhibitor is selected from the list consisting of flavopiridol, ribocilib, staurosporine/UCN-01, abemaciclib and palbociclib, and any combination thereof. In certain embodiments, the cell cycle inhibitor is selected from the list consisting of flavopiridol, ribocilib, staurosporine/UCN-01, abemaciclib and palbociclib, and any combination thereof.

In another embodiment, the 6-β-naltrexol is for use in the treatment of a subject having lung cancer, wherein the subject is undergoing or is selected to undergo treatment with a cell cycle inhibitor or an agent that induces cytostasis. The ability of 6-β-naltrexol to induce cytostasis is likely to have a particularly beneficial effect upon the therapeutic efficacy of anti-cancer agents that are cell cycle inhibitors. As defined herein, "cytostasis" refers to the inhibition of cell growth and proliferation. Cell cycle inhibitors function by inhibiting the activity of cellular factors that directly or indirectly promote the progression of the cell cycle. A non-limiting example of a cell cycle inhibitor is a DNA topoisomerase inhibitor. DNA topoisomerases are responsible for unwinding and rewinding of DNA during DNA replication and repair. The inhibition of DNA topoisomerases thus precludes the replication of the DNA and induces cytostasis. The adverse metabolic profile of the cancer cell may subsequently activate DNA-damage response pathways due to the accumulation of DNA mutations that go unrepaired. The activation of DNA damage response pathways ultimately activates pro-apoptotic cascades within the cancer cell, leading to cancer cell death. Thus, cytostasis caused by cell cycle inhibitors is linked to the subsequent cytotoxic activity of the inhibitor. Further boosting cytostasis by administration of a cell cycle inhibitor alongside 6-β-naltrexol will further enhance the cytotoxic effect of this class of anti-cancer agents. It is envisaged that this beneficial effect is applicable to all anti-cancer agents that are cell cycle inhibitors, and all agents that induce cytostasis.

In another embodiment, the cell cycle inhibitor is selected from the group consisting of flavopiridol, ribocilib, staurosporine/UCN-01, abemaciclib and palbociclib, and any combination thereof.

As used herein, the "term cancer cell" refers to a cell or immortalized cell line derived from a tumour or cancer.

The 6-β-naltrexol is to be administered to the subject in need thereof in a first treatment phase, either alone or in conjunction with vitamin D, followed by a recovery period, wherein, following the recovery period, the subject is to be administered the anti-cancer agent, the recovery period being characterised by the absence of administration of 6-β-naltrexol and the anti-cancer agent. The use of a recovery period as opposed to continuous administration is likely to cause a greater reduction in cell numbers when compared with continuous administration. The inhibition of cell growth and proliferation during the first treatment phase will synchronise the phase of the cell cycle within which the tumour cells reside. The subsequent recovery period will allow for a temporary reprieve of cytostasis. The subsequent administration of the anti-cancer agent will ultimately cause cytotoxicity. Without wishing to be bound by theory, it is thought that by synchronising the cancer cells at a particular stage in the cell cycle, 6-β-naltrexol will allow the anti-cancer agent to act on cells in an aligned state, thereby increasing sensitivity. Certain cellular processes that are arrested during cytostasis are desirable for achieving apoptosis, thus continual cytostasis may prevent the maximum cytotoxic effect of the anti-cancer agent from being realised.

In a further aspect, the recovery period is from 1 to 7 days. In another embodiment, the recovery period is from 2 to 5 days. In another embodiment, the recovery period is from 3 to 5 days.

In another embodiment, the 6-β-naltrexol is to be administered at a dosage level sufficient to raise the blood plasma concentration of 6-β-naltrexol to within from 0.34 ng/ml to 3,400 ng/ml, preferably from 0.34 ng/ml to 340 ng/ml. Most preferably in 6-β-naltrexol to is be administered at a dosage level sufficient to increase the blood plasma concentration of 6-β-naltrexol to within from 0.34 ng/ml to 34 ng/ml. Methods for measuring the 6-β-naltrexol concentration in a plasma sample obtained from a subject undergoing administration of 6-β-naltrexol will be well known to the person skilled in the art. Non-limiting examples of such methods include, mass spectrometry, nuclear magnetic resonance spectrometry, IR spectroscopy, or gas or liquid phase chromatography.

In a second aspect of the invention, there is provided a method for the treatment of a subject with lung cancer comprising administering a therapeutically effective amount of 6-β-naltrexol, wherein the subject is also administered vitamin D or an active metabolite thereof.

The term "therapeutically effective amount" refers to an amount of 6-β-naltrexol or an analogue thereof or a pharmaceutically acceptable salt of either, that preferably results in a decrease in severity of disease symptoms, an increase in frequency and duration of disease symptom-free periods, or a prevention of impairment or disability due to the disease affliction. The terms "effective amount" or "pharmaceutically effective amount" refer to a sufficient amount of an agent to provide the desired biological or therapeutic result. That result can be reduction, amelioration, palliation, lessening, delaying, and/or alleviation of one or more of the signs, symptoms, or causes of a disease, or any other desired alteration of a biological system. In reference to cancer, an effective amount may comprise an amount sufficient to cause a tumour to shrink and/or to decrease the growth rate of the tumour (such as to suppress tumour growth) or to prevent or delay other unwanted cell proliferation. In some embodiments, an effective amount is an amount sufficient to delay development, or prolong survival or induce stabilisation of the cancer or tumour.

In some embodiments, a therapeutically effective amount is an amount sufficient to prevent or delay recurrence. A therapeutically effective amount can be administered in one or more administrations. The therapeutically effective amount of the therapeutic preparation or preparations may result in one or more of the following: (i) reduce the number of cancer cells; (ii) reduce tumour size; (iii) inhibit, retard, slow to some extent and preferably stop cancer cell infiltration into peripheral organs; (iv) inhibit (i.e., slow to some extent and preferably stop) tumour metastasis; (v) inhibit tumour growth; (vi) prevent or delay occurrence and/or recurrence of tumour; and/or (vii) relieve to some extent one or more of the symptoms associated with the cancer.

For example, for the treatment of tumours, a "therapeutically effective dosage" may induce tumour shrinkage by at least about 5% relative to baseline measurement, such as at least about 10%, or about 20%, or about 60% or more. The baseline measurement may be derived from untreated subjects. A therapeutically effective amount of a therapeutic preparation or preparations can decrease the severity of symptoms, or otherwise ameliorate symptoms in a subject. One of ordinary skill in the art would be able to determine such amounts based on such factors as the subject's size, the severity of the subject's symptoms, and the particular composition or route of administration selected.

In certain embodiments, the method is for treatment of lung cancer in a subject undergoing treatment with an anti-cancer agent. Preferably, the anti-cancer agent is a cell cycle inhibitor or an agent that induces cytostasis.

In certain embodiments, the cell cycle inhibitor is selected from the group consisting of flavopiridol, ribocilib, staurosporine/UCN-01, abemaciclib and palbociclib, and any combination thereof.

In certain embodiments of the second aspect of the invention, the method is for the treatment of lung cancer is a subject, wherein the subject is to be administered vitamin D or an active metabolite thereof concurrently. The vitamin D and 6-β-naltrexol may be administered separately, simultaneously or sequentially.

In certain embodiments, the 6-β-naltrexol and vitamin D product are to be administered simultaneously.

In certain embodiments, 6-β-naltrexol is to be administered at a dosage level of sufficient to raise the blood plasma concentration of 6-β-naltrexol to about from 0.34 ng.ml to 3,400 ng/ml, preferably to about from 0.34 ng/ml to 340 ng/ml.

In certain embodiments, the 6-β-naltrexol is to be administered in a first treatment phase, followed by a recovery period, and the anti-cancer agent is to be administered in a second treatment phase following the recovery period, wherein the recovery period is characterised by the lack of administration of either 6-β-naltrexol or the anti-cancer agent.

For use in the invention, there is provided a pharmaceutical composition comprising 6-β-naltrexol or an analogue thereof or a pharmaceutically acceptable salt of either in a combined formulation with vitamin D or an active metabolite thereof or a pharmaceutically acceptable salt of either. The pharmaceutical composition may be provided as an oral solution, a caplet, a capsule, an injectable, an infusible, a suppository, a lozenge or a tablet. In certain embodiments, the pharmaceutical composition is provided in oral dosage forms, particularly as a tablet.

As used herein the term "pharmaceutical composition" means, for example, a mixture containing a specified amount of a therapeutic compound or compounds, e.g. a therapeutically effective amount, in a pharmaceutically acceptable carrier to be administered to a mammal, e.g., a human in order to treat a disease.

As used herein the term "pharmaceutically acceptable" refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

The term formulation is intended to include the mixture of the active component(s) with encapsulating material as a carrier providing a solid dosage form in which the active compound (with or without other carriers) is surrounded by a carrier which is thus in association with it. Similarly, cachets are included. Tablets, powders, cachets, and capsules can be used as solid dosage forms suitable for oral administration.

The pharmaceutical formulation can be in unit dosage form. In such form, the composition is divided into unit doses containing appropriate quantities of the active component(s). The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

In one embodiment, the vitamin D product is to be employed in the present compositions in a range of about 400 IU to about 10,000 IU per dosage form. Further, the compositions of the present invention may comprise from 0.01% to 25% by weight of the composition of the vitamin D product, preferably from about 0.1% to 20% by weight of the composition of the vitamin D product, more preferably from about 0.5% to 10% by weight of the composition of the vitamin D product. In another embodiment of the invention, the composition comprises the appropriate amount of dosages of the vitamin D product to account for the degradation, if any, of the vitamin D product.

In one embodiment, the 6-β-naltrexol product to be employed in the present compositions in a solid oral dosage form contains a therapeutically effective amount of 6-β-naltrexol, which may be, for example, from about 0.01 mg to up to 50 mg, preferably from about 0.01 mg to about 40 mg, most preferably from about 0.01 to about 20 mg of the 6-β-naltrexol product per tablet; e.g. about 0.01 mg, about 0.05 mg, about 0.1 mg, about 0.3 mg, about 0.5 mg, about 1 mg, about 2 mg, about 3 mg, about 5 mg, about 10 mg, about 20 mg, about 30 mg, about 40 mg or about 50 mg of the 6-β-naltrexol product per tablet. In certain embodiments, the composition comprises the appropriate amount of dosages of the 6-β-naltrexol product to account for degradation, if any, of the 6-β-naltrexol product. In certain embodiments the composition comprises of from 3 mg to 4.5 mg.

The pharmaceutical composition may be provided as a blend of both the vitamin D product and the 6-β-naltrexol product and a combination of pharmaceutically acceptable excipients. As used herein, the term "excipient" refers to a pharmaceutically acceptable ingredient that is commonly used in pharmaceutical technology for the preparation of solid oral dosage formulations. Examples of categories of excipients include, but are not limited to, binders, disntegrants, lubricants, glidants, stabilizers, fillers, and diluents. The amount of each excipient used may vary within ranges conventional in the art. The following references which are all hereby incorporated by reference disclose techniques and excipients used to formulate oral dosage forms. See The Handbook of Pharmaceutical Excipients, 4th edition, Rowe et al., Eds., American Pharmaceuticals Association (2003); and Remington: the Science and Practice of Pharmacy, 20th edition, Gennaro, Ed., Lippincott Williams & Wilkins (2000).

Suitable excipients include magnesium carbonate, magnesium stearate, talc, lactose, lactose monohydrate, sugar, pectin, dextrin, starch, tragacanth, microcrystalline cellulose, methyl cellulose, sodium carboxymethyl cellulose, corn starch, colloidal anhydrous Silica, titanium dioxide, a low-melting wax, cocoa butter, and the like.

In another embodiment, the pharmaceutical composition comprises at least one excipient.

According to all aspects of the invention, the tumours/cancers include, but are not limited to, those comprising small-cell lung cancer, non-small cell lung cancer, adenocarcinoma of the lung and squamous carcinoma of the lung. The invention is illustrated by the following non-limiting examples.

EXAMPLES

Example 1

Administration of Low Dose 6-β-naltrexol or CCT to Lung and Colorectal Cancer Cells The cytostatic effect upon administration of 6-β-naltrexol (6BN) and naltrexone (NTX) to A549 (lung cancer) and HCT116 (colorectal cancer) cells was studied in vitro. Firstly, A549 and HCT116 cells were seeded into 6-well plates at a density of $2 \times 10^5$/well and left to adhere overnight. Cells were then cultured with 0.001 µM, 0.01 µM, 0.1 µM or 1 µM of 6BN or NTX for 48 hours. Experiments were performed alongside a control where cells were not administered with 6-β-naltrexol or naltrexone (FIG. 1).

The viability of cells was then measured by cell counting using trypan blue as a way of discriminating live and dead cells. Cytostasis was indicated by a reduction in cell number and no associated reduction in cell viability.

The experiment shows that administration of 6-β-naltrexol results in a selective reduction in cytotostasis in lung cancer cells, and a less pronounced decrease in cytotostasis when administered at higher concentrations to colorectal cancer cells. No reduction in cell viability was observed.

Example 2

Administration of Low Dose 6-β-naltrexol or LDN in Combination with CTT

Next, the effect of co-administration of low dose (10 nM) or high dose (10 µM) 6-β-naltrexol or naltrexone (NTX) alongside calcitriol was investigated. The cytostatic and cytotoxic effect was investigated in both A549 and HCT116 cells. A549 and HCT116 cells were seeded into 6-well plates at a density of $2 \times 10^5$/well and left to adhere overnight. The following day low or high dose 6BN or NTX was added to cells in isolation or in combination with calcitriol and incubated for 48 hours. A549 cells were co-administered with 10 nM calcitriol, whereas HCCT116 cells were co-administered 10 nM calcitriol.

Cell viability and cytostasis were then determined as described in example 1.

Figure 2:
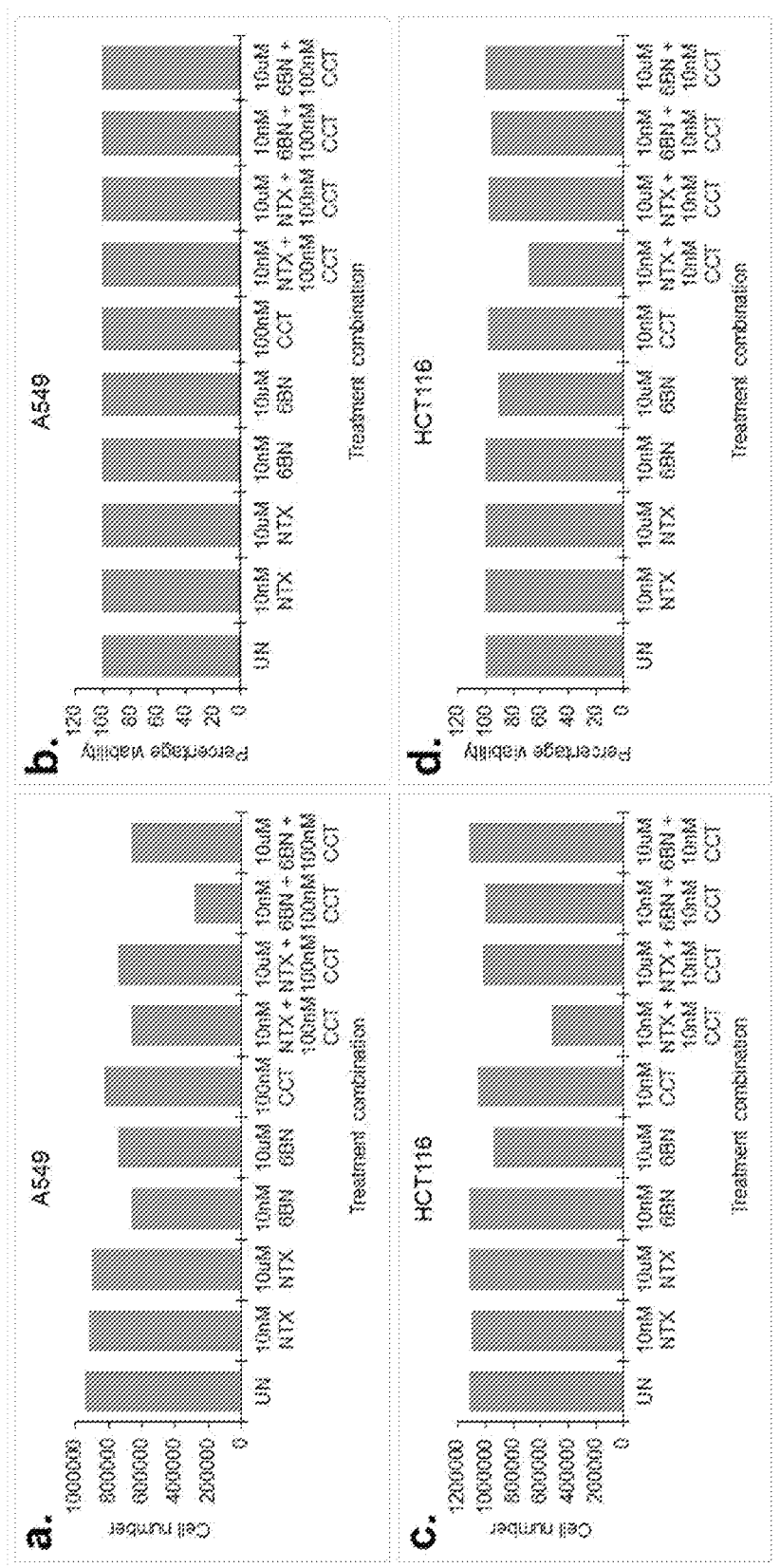
FIG. 2 shows the effect on cell number (a and b) and cell viability (c and d) in A549 (lung cancer) and HCT116 (colorectal cancer) cell lines upon administration of 10 nM NTX (LDN), 10 µM NTX, 10 nM 6BN, 10 µM 6BN, 100 nM calcitriol (CCT), or 10 nM NTX (LDN), 10 µM NTX, 10 nM 6BN or 10 µM 6BN in combination with CCT. Experiments were performed alongside a control where cells were not administered with 6BN, NTX, or CCT (UN).

The experiments show that upon co-administration with calcitriol A549 cells treated with 10 nM 6BN show a significant reduction in cytostasis. The equivalent effect is not observed in HCCT116 cells, or when calcitriol is administered alongside 10 µM 6BN (FIG. 2). Furthermore, the results show that the combination of 10 nM NTX with 100 nM calcitriol reduces the viability of HCCT116 cells. The reduction in cell number is achieved by cytotoxicity, as opposed to cytostasis, thus demonstrating that the combination of 6BN and calcitriol achieves a therapeutic effect via a distinct mechanism to NTX.

The invention claimed is:

1. A method of treating lung cancer comprising administering 6-β-naltrexol sequentially, separately or simultaneously with vitamin D or an active metabolite thereof to a subject having lung cancer.

2. The method of claim 1, wherein the subject is undergoing or is selected to undergo treatment with an anti-cancer agent.

3. The method of claim 1, wherein said 6-β-naltrexol is to be administered to the subject in need thereof in a first treatment phase, followed by a recovery period, then subsequent administration of an anti-cancer agent in a second treatment phase.

4. The method of claim 3, wherein the recovery period is from 1 to 7 days.

5. The method of claim 2, wherein the 6-β-naltrexol and anti-cancer agent are to be administered simultaneously.

6. The method of any of claims 2 to 5, wherein the anti-cancer agent is a cell cycle inhibitor or an agent that induces cytostasis.

7. The method of claim 6, wherein the cell cycle inhibitor is selected from the group consisting of flavopiridol, ribociclib, staurosporine, UCN-01, abemaciclib and palbociclib, and any combination thereof.

8. The method of claim 1, wherein the 6-β-naltrexol is to be administered at a dosage level sufficient to raise the blood plasma concentration of 6-β-naltrexol to about from 0.34 ng/ml to 3,400 ng/ml.

9. A method for the treatment of a subject with lung cancer, comprising administering a therapeutically effective amount of 6-β-naltrexol, wherein the subject is also administered vitamin D or an active metabolite thereof.

10. A method according to claim 9, wherein the subject is undergoing or is selected to undergo treatment with an anti-cancer agent.

11. A method according to claim 10, wherein said anti-cancer agent is a cell cycle inhibitor or an agent that induces cytostasis.

12. A method according to claim 11, wherein said cell cycle inhibitor is selected from the group consisting of flavopiridol, ribociclib, staurosporine, UCN-01, abemaciclib and palbociclib, and any combination thereof.

13. A method according to any of claims 9 to 12, wherein said 6-β-naltrexol is administered at a dosage level of less than sufficient to raise the blood plasma concentration of 6-β-naltrexol to about from 0.34 ng/ml to 3,400 ng/ml.

14. The method of any of claims 1 to 5, wherein the Vitamin D or the active metabolite thereof is administered in a dose sufficient to raise the Vitamin D blood concentration from 0.34 ng/ml to 3,400 ng/ml.

* * * * *